(12) United States Patent
Yamaguchi et al.

(10) Patent No.: US 10,751,937 B2
(45) Date of Patent: Aug. 25, 2020

(54) LAYER LAMINATING MOLDED OBJECT, POWDER LAYER LAMINATING MOLDING METHOD, AND RIDGE FILTER

(71) Applicant: Hitachi, Ltd., Chiyoda-ku, Tokyo (JP)

(72) Inventors: Akihiro Yamaguchi, Tokyo (JP); Satoshi Arai, Tokyo (JP); Shigeharu Tsunoda, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 60 days.

(21) Appl. No.: 15/881,105

(22) Filed: Jan. 26, 2018

(65) Prior Publication Data

US 2018/0222113 A1    Aug. 9, 2018

(30) Foreign Application Priority Data

Feb. 9, 2017   (JP) ................... 2017-022187

(51) Int. Cl.
| | |
|---|---|
| *B29C 64/153* | (2017.01) |
| *B29C 64/393* | (2017.01) |
| *B33Y 10/00* | (2015.01) |
| *B33Y 80/00* | (2015.01) |
| *B33Y 50/02* | (2015.01) |
| *A61N 5/10* | (2006.01) |
| *B29L 11/00* | (2006.01) |

(52) U.S. Cl.
CPC .......... *B29C 64/153* (2017.08); *B29C 64/393* (2017.08); *A61N 5/10* (2013.01); *A61N 2005/1095* (2013.01); *B29L 2011/0066* (2013.01); *B33Y 10/00* (2014.12); *B33Y 50/02* (2014.12); *B33Y 80/00* (2014.12)

(58) Field of Classification Search
CPC ............... B29C 64/153; B29C 64/393; G05B 2219/49023; B33Y 10/00; B33Y 50/02; B33Y 80/00; A61N 5/10; B22F 3/1055
See application file for complete search history.

(56) References Cited

U.S. PATENT DOCUMENTS

| | | |
|---|---|---|
| 2003/0127436 A1 | 7/2003 | Darrah et al. |
| 2016/0243805 A1 | 8/2016 | Satoh |
| 2016/0282848 A1* | 9/2016 | Hellestam .......... G05B 19/4099 |

FOREIGN PATENT DOCUMENTS

| | | |
|---|---|---|
| JP | 2003-136604 A | 5/2003 |
| JP | 2010-228332 A | 10/2010 |
| JP | 2016-155367 A | 9/2016 |

OTHER PUBLICATIONS

Japanese-language Office Action issued in Japanese Application No. 2017-022187 dated Mar. 24, 2020 with English translation (five (5) pages).

* cited by examiner

*Primary Examiner* — Catherine A. Simone
(74) *Attorney, Agent, or Firm* — Crowell & Moring LLP

(57) ABSTRACT

The present invention prevents warp deformation of a molded object formed by laser powder layer laminating molding. There is provided a powder layer laminating molding method including a first step of forming a powder layer which includes powder of a thermoplastic resin, and a second step of sintering the powder layer by irradiating the formed powder layer with a beam having a heating action, in which a molded object is obtained by repeatedly performing the forming and the sintering of the powder layer in the first step and the second step, and an irradiation surface which is irradiated with the beam is divided into a plurality of small regions.

6 Claims, 17 Drawing Sheets

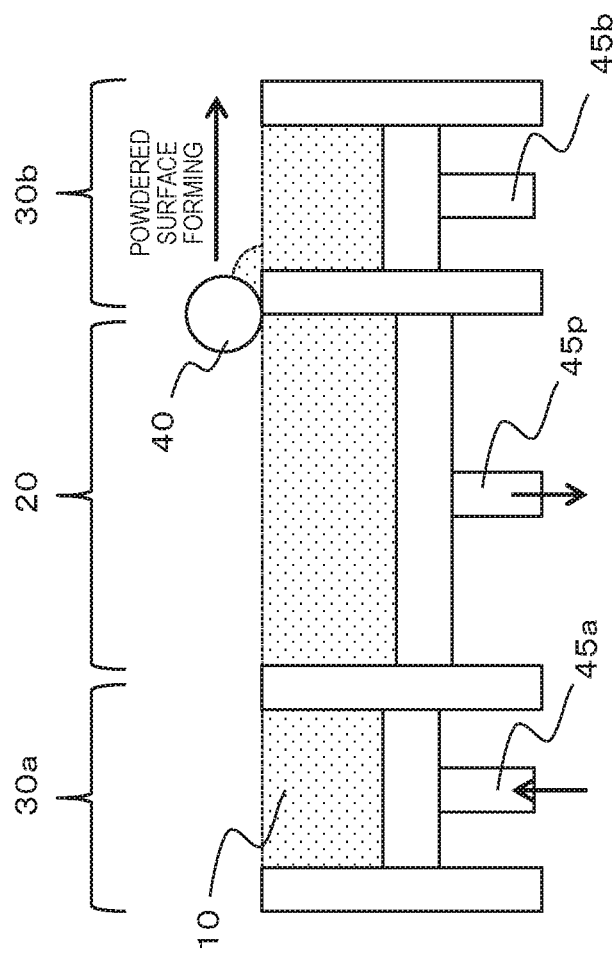

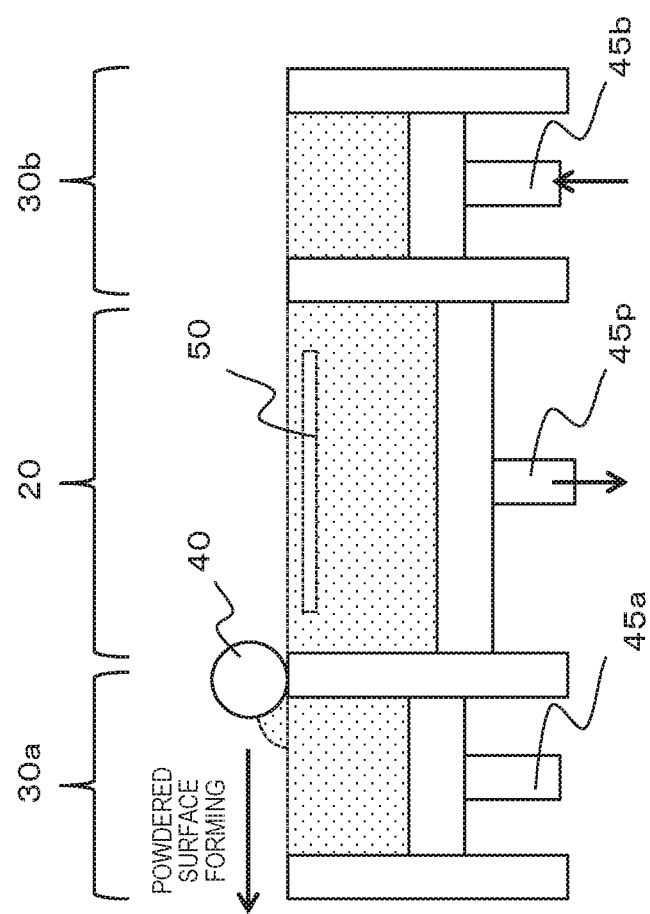

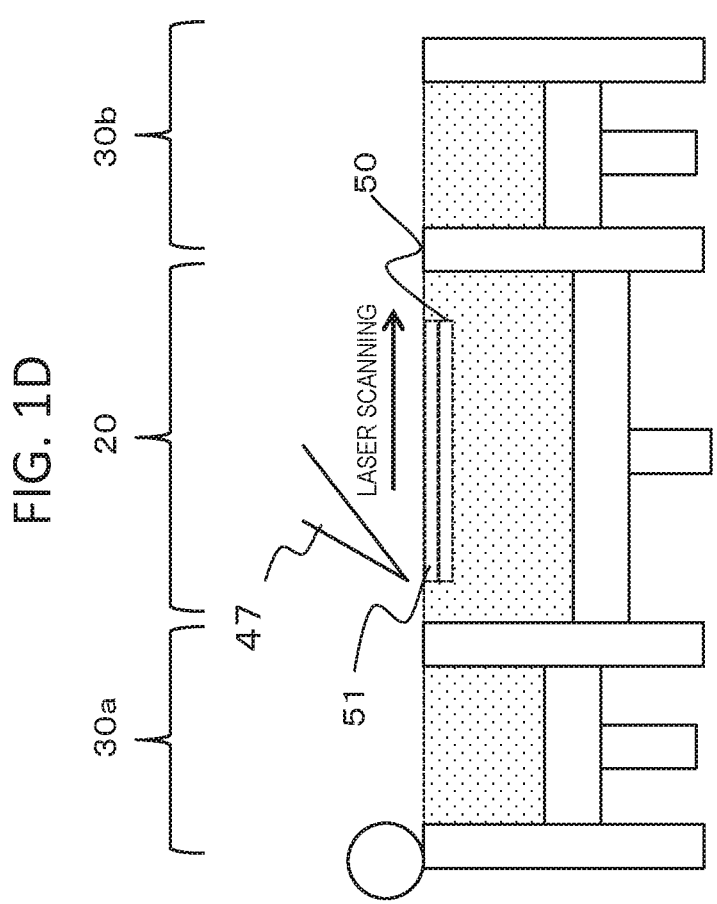

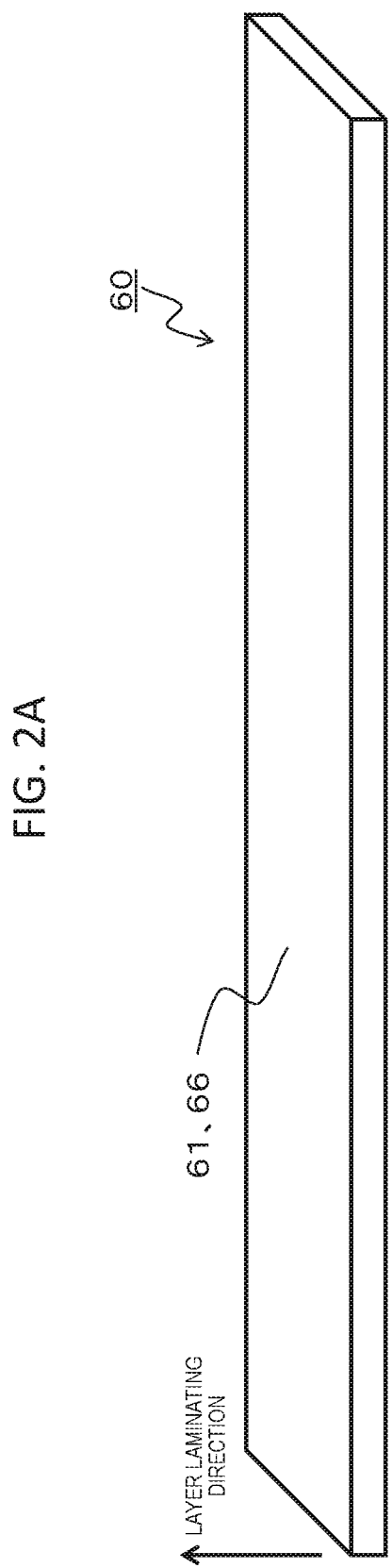

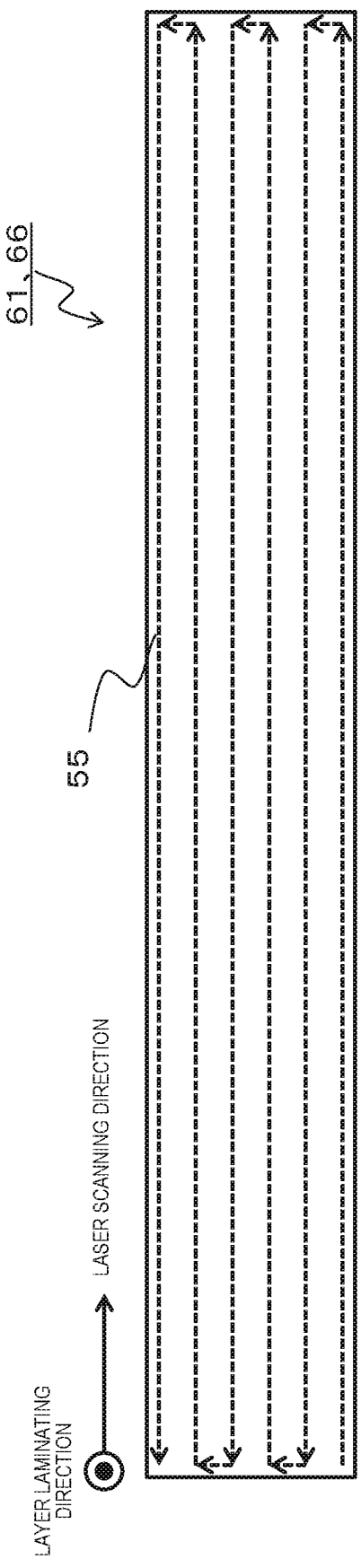

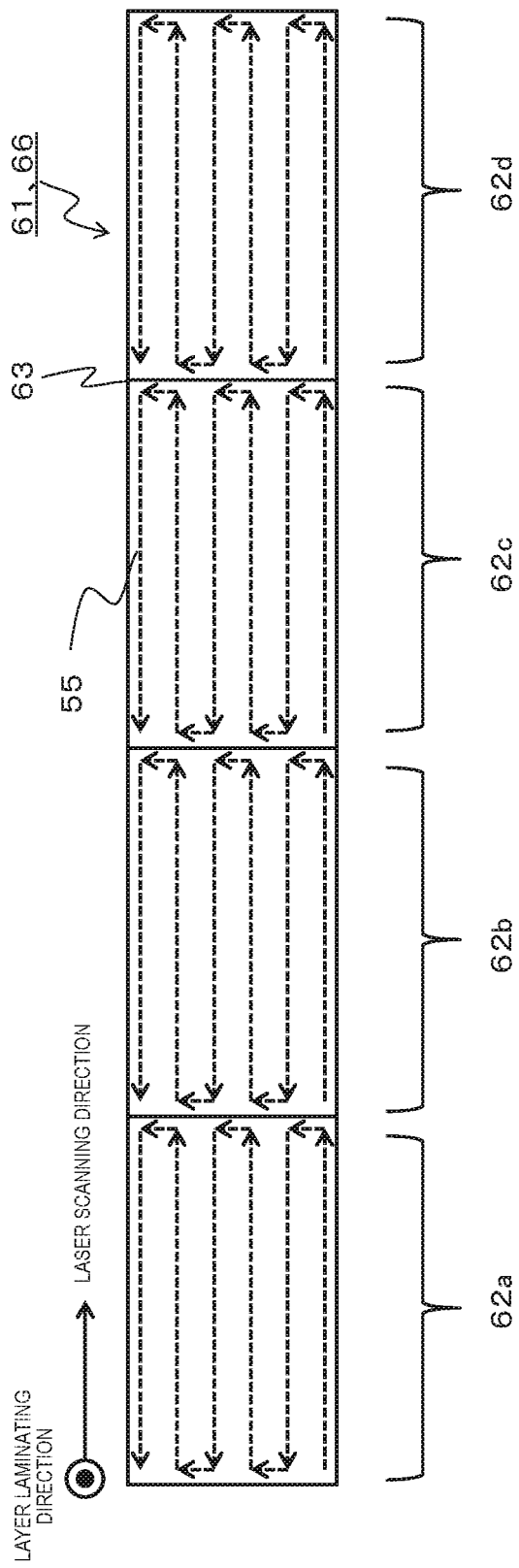

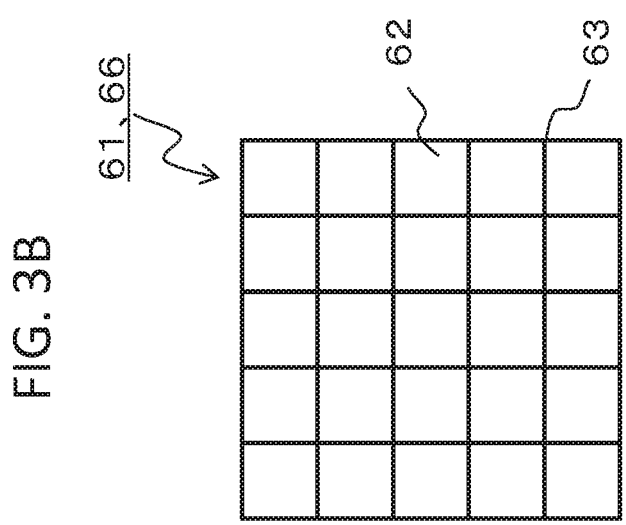

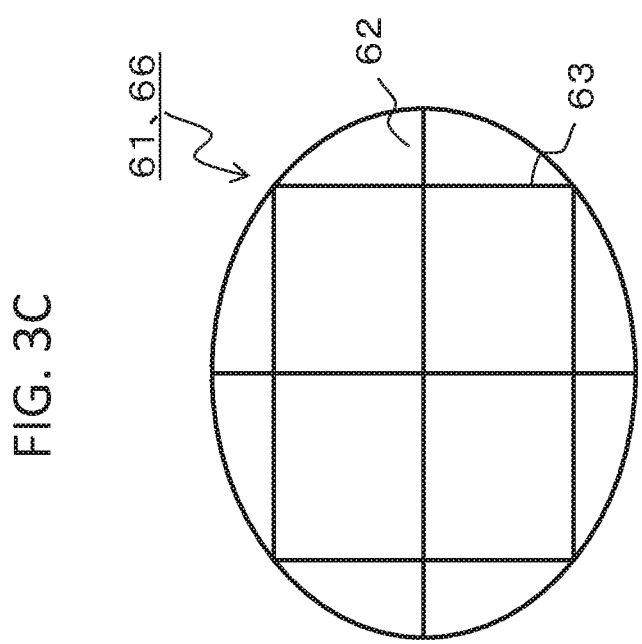

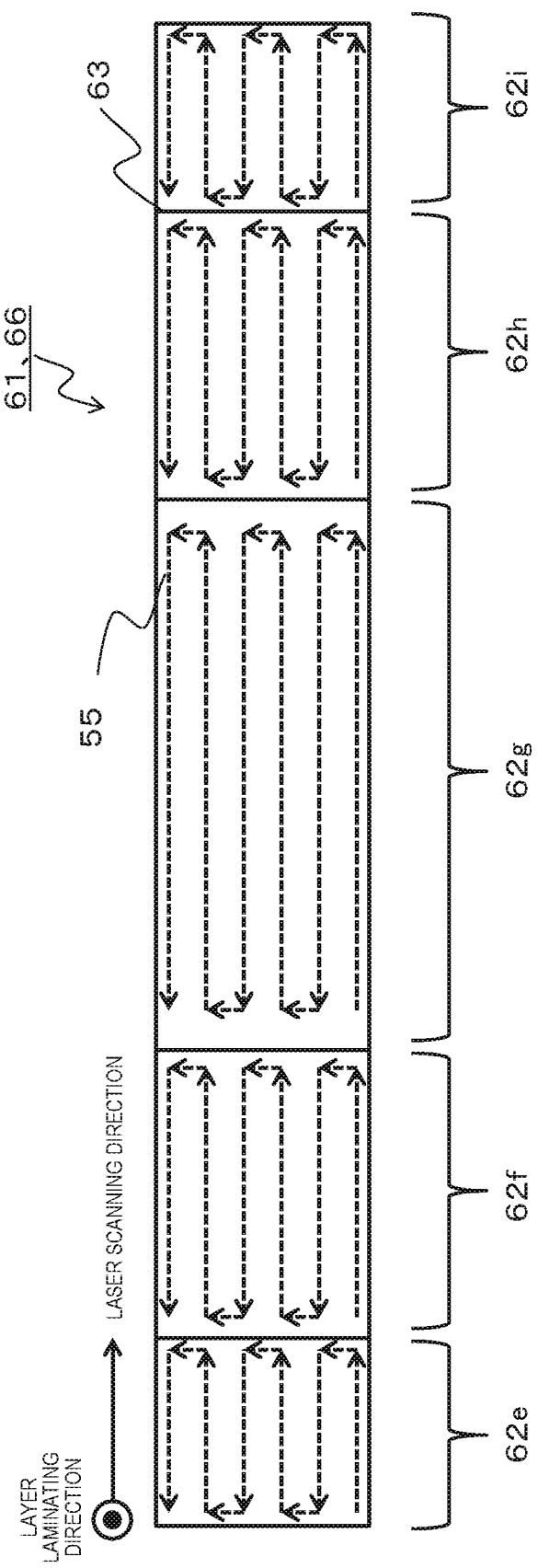

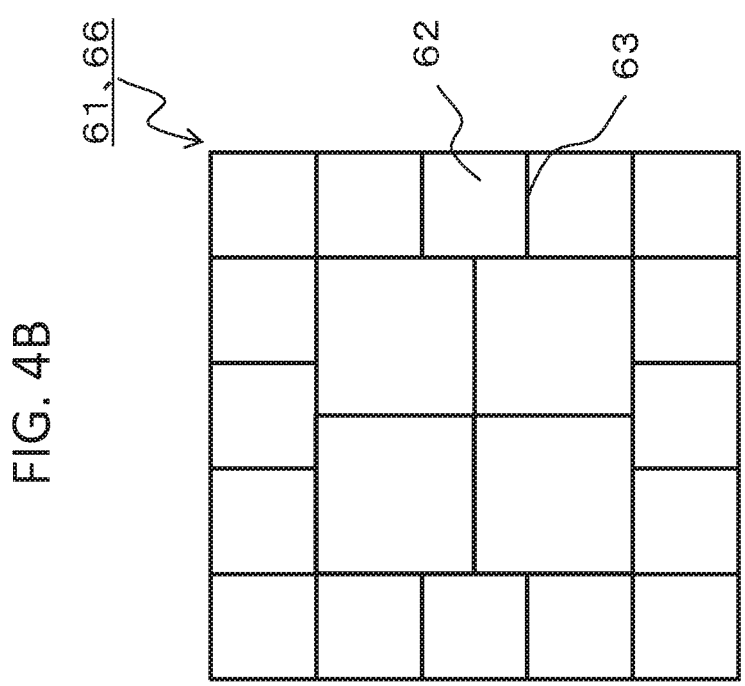

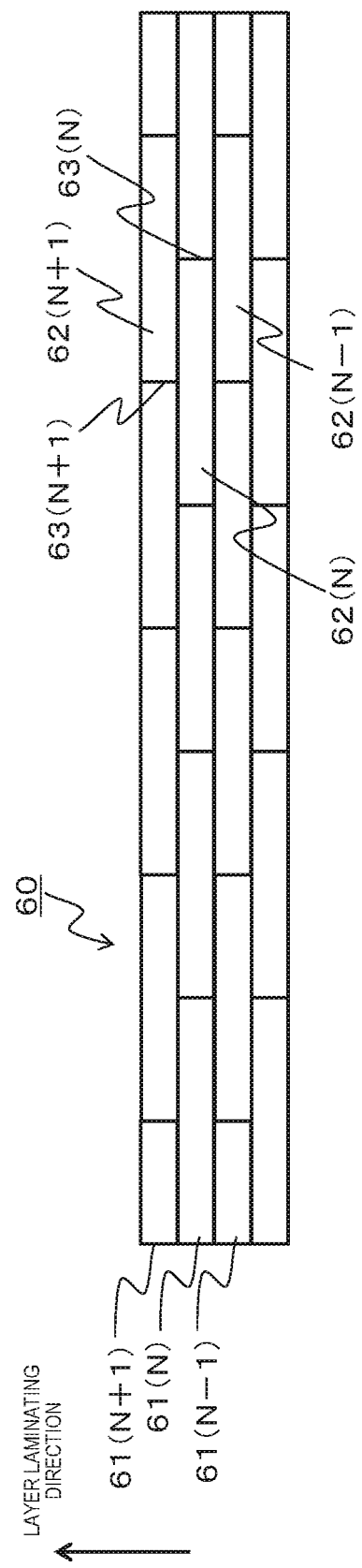

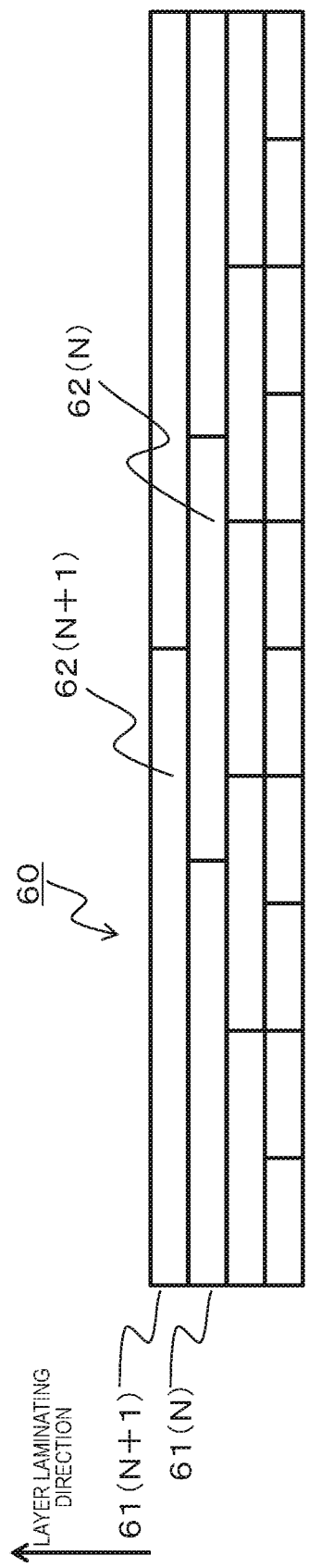

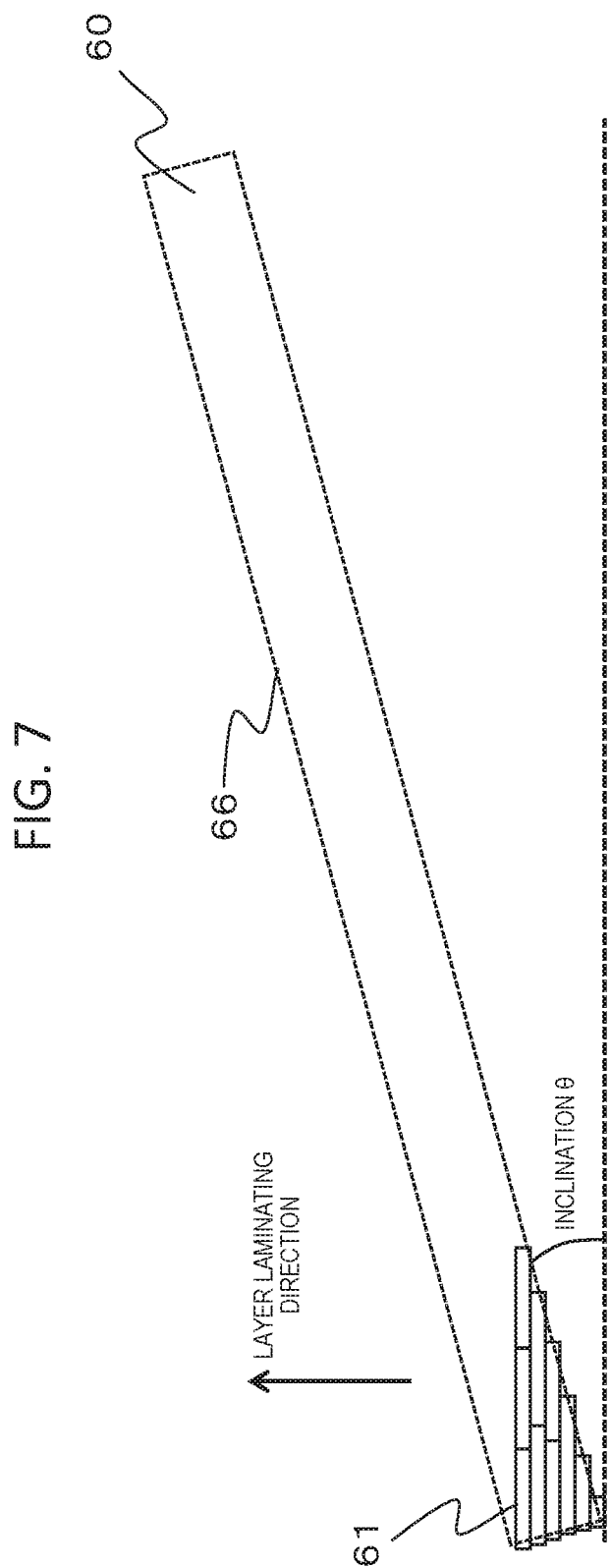

LAYER LAMINATING MOLDED OBJECT, POWDER LAYER LAMINATING MOLDING METHOD, AND RIDGE FILTER

TECHNICAL FIELD

The present invention relates to a technology relating to a powder layer laminating molded object which is formed using a laser or the like.

BACKGROUND ART

As a background art in the present technical field, there is JP-A-2016-155367 (PTL 1). In PTL 1, "a three-dimensional molding method for molding a three-dimensional molded object by laminating layers of a layer-shaped molded object obtained by combining pulverulent bodies of a pulverulent body layer with each other, in which when a lower surface of a molding region of the layer-shaped molded object is formed while being in contact with the pulverulent body, a sacrifice molded object that is separable from the three-dimensional molded object through the pulverulent body, is formed below the molding region where the lower surface is formed while being in contact with the pulverulent body" is disclosed.

CITATION LIST

Patent Literature

PTL 1: JP-A-2016-155367

SUMMARY OF INVENTION

Technical Problem

PTL 1 discloses a method in which the three-dimensional molded object is molded by separating the sacrifice molded object from the molded object when the three-dimensional molded object is molded by a powder layer laminating molding method. However, in the method disclosed in PTL 1, it is not possible to prevent warp deformation of the molded object which is generated due to contraction of a material at the time of laser powder layer laminating molding.

Solution to Problem

According to an aspect of the present invention, there is provided a layer laminating molded object which has a layer laminating structure of a sintered body layer of thermoplastic resin powder, in which the sintered body layer is divided into a plurality of small regions within a surface of the layer.

According to another aspect of the present invention, there is provided a powder layer laminating molding method including a first step of forming a powder layer which includes powder of a thermoplastic resin, and a second step of sintering the powder layer by irradiating the formed powder layer with a beam having a heating action, in which a molded object is obtained by repeatedly performing the forming and the sintering of the powder layer in the first step and the second step, and an irradiation surface which is irradiated with the beam is divided into a plurality of small regions.

According to still another aspect of the present invention, there is provided a ridge filter which is provided in a particle therapy system, including a first structure body that includes a plurality of extending portions which extend along an injection direction of a particle beam used in the particle therapy system, and a second structure body that is provided with one of a first surface of the first structure body on an injection side of the particle beam and a second surface which is an opposite side to the first surface, in which the first structure body and the second structure body are integrally formed, and each of the first structure body and the second structure body includes a layer laminating body.

Advantageous Effects of Invention

According to the present invention, it is possible to prevent the warp deformation of the molded object which is generated at the time of the laser powder layer laminating molding.

BRIEF DESCRIPTION OF DRAWINGS

FIG. 1A is a side view illustrating an outline of a first-time powdered surface forming treatment of a laser powder layer laminating molding method.

FIG. 1C is a side view illustrating an outline of a second-time powdered surface forming treatment of the laser powder layer laminating molding method.

FIG. 1D is a side view illustrating an outline of a second-time laser scanning treatment of the laser powder layer laminating molding method.

FIG. 2A is a perspective view illustrating an example of a layer laminating structure object.

FIG. 2B is a top view illustrating an example of a laser scanning path in the related art.

FIG. 3A is a top view illustrating an example of a laser scanning path according to Example 1.

FIG. 3B is a top view for describing a structure of a molded object according to Example 1.

FIG. 3C is a top view for describing the structure of the molded object according to Example 1.

FIG. 4A is a top view illustrating an example of a laser scanning path according to Example 2.

FIG. 4B is a top view for describing a structure of a molded object according to Example 2.

FIG. 5 is a side view for describing a structure of a molded object according to Example 3.

FIG. 6 is a side view for describing a structure of a molded object according to Example 4.

FIG. 7 is a side view for describing a structure and a molding method of a molded object according to Example 5.

DESCRIPTION OF EXAMPLES

Figure 1B:
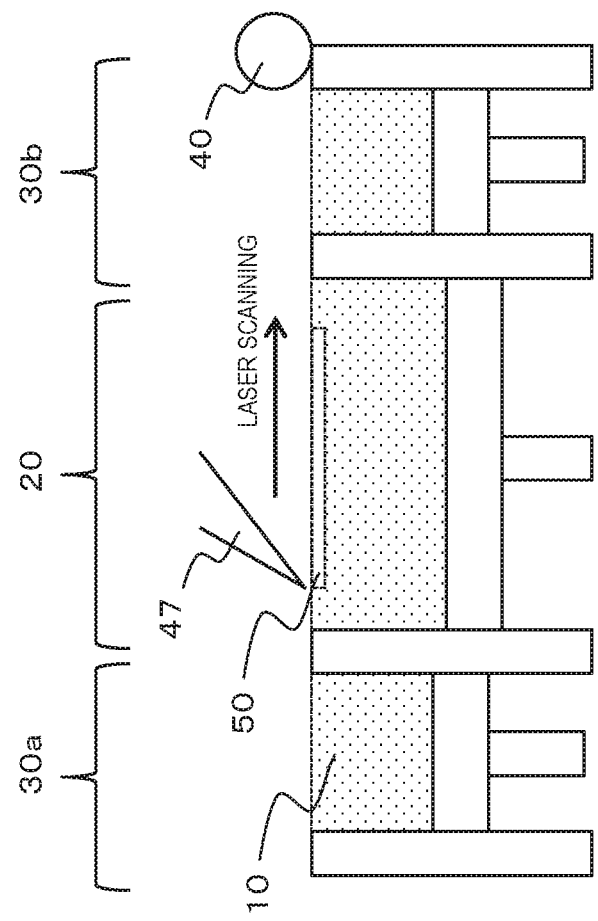
FIG. 1B is a side view illustrating an outline of a first-time laser scanning treatment of the laser powder layer laminating molding method.

Embodiments will be described in detail using the drawings. However, the present invention is not understood as being limited to the description of the embodiments described hereinafter. It is easily understood by the inventors of the present invention to obtain a specific configuration thereof by modify the specific configuration, within a scope without departing from the idea or the gist of the present invention.

In the configuration of the invention described hereinafter, the same reference signs are used for the same portions or portions having similar functions in common between the drawings which are different from each other, and the repeated description thereof will be omitted.

In the present specification, notations such as "first", "second", and "third" are attached in order to identify components, and do not necessarily limit the number thereof or a sequence. A numeral for identifying the component is used per context, and the numeral used in one context is not limited to necessarily indicate the same configuration in other contexts. It is not interrupted that the component identified by a certain numeral serves as the functions of the components identified by other numerals.

A position, a size, a shape, a scope, and the like of each configuration illustrated in the drawings are made in order to easily understand the invention, and there is a case where the actual position, the actual size, the actual shape, the actual scope, and the like are not represented. Therefore, the present invention is not necessarily limited to the position, the size, the shape, the scope, and the like disclosed in the drawings.

Example 1

Example 1 will be described using FIG. 1, FIG. 2, and FIG. 3. FIGS. 1A to 1D are diagrams illustrating an outline of a laser powder layer laminating molding method, FIGS. 2A and 2B are diagrams illustrating an example of a molded object and a laser scanning path in the related art, and FIG. 3 is a diagram for describing a structure and a molding method of a molded object according to Example 1.

In Example 1, the laser powder layer laminating molding method illustrated in FIG. 3A is used, as a molding method of a plate-shaped layer laminating molded object which is illustrated as an example in FIG. 2A. The laser powder layer laminating molding method is a method in which powder of a thermoplastic resin is laid using a roller or a blade, the laid powder is irradiated with a laser, and melting and sintering are performed, thereby, layers are laminated and molded. In the laser powder layer laminating molding method, it is possible to manufacture (mold) a three-dimensional object in one body of which the molding time is long, and it is possible to manufacture even the shape which is less likely to be manufactured in mechanical machining.

FIG. 1A is a side view illustrating a first-time powdered surface forming treatment of the laser powder layer laminating molding method. In the laser powder layer laminating molding method, first, as illustrated in FIG. 1A, a piston 45a of a left side feed portion 30a in which material powder 10 is stored is raised, and the material powder 10 thereof is pushed up. A piston 45p of a part bed portion 20 is dropped, and a surface of the material powder 10 thereof is dropped. Therefrom, using a roller 40, the material powder 10 is supplied and laid to the part bed portion 20.

FIG. 1B is a diagram illustrating a first-time laser scanning treatment. The material powder 10 is melted and sintered by irradiating the laid material powder 10 with a laser 47 from a laser light source, and a sintered body 50 of a first layer is obtained.

FIG. 1C is a diagram illustrating a second-time powdered surface forming treatment. Using the roller 40 again, a piston 45b of a right side feed portion 30b is raised in the same manner as that of FIG. 1A, the material powder 10 is pushed up, the piston 45p of the part bed portion 20 is dropped, and the surface of the material powder 10 is dropped, therefrom, the material powder 10 is supplied and laid onto the sintered body 50 of the first layer of the part bed portion 20.

FIG. 1D is a diagram illustrating a second-time laser scanning treatment. The material powder 10 is melted and sintered by irradiating the laid material powder 10 with the laser 47 from the laser light source, and a sintered body 51 of a second layer is obtained by being combined with the sintered body of the first layer. By repeating such steps, layers of an arbitrary three-dimensional structure object are laminated and molded. In the laser powder layer laminating molding method, from the viewpoint of accuracy and strength, a crystalline resin is generally used, and PA12 (polyamide 12), PA 11 (polyamide 11), PP (polypropylene), PE (polyethylene), POP (polyoxymethylene) PBT (polybutylene terephthalate) PA6 (polyamide 6), PA6-6 (polyamide 6-6), PPS, PEEK, or the like may be used as a target. However, as long as the crystalline resin is a main material, an alloy or a blend with a non-crystalline resin may be used as a target.

FIGS. 2A and 2B are diagrams illustrating an example of the shape of the molded object and the scanning path in the laser scanning treatment of the related art.

FIG. 2A illustrates a perspective view of a plate-shaped layer laminating molded object 60 which is formed. In general, a laser irradiation surface 61 of the plate-shaped layer laminating molded object 60 is the same as a surface 66 (referred to as a "wide surface", hereinafter) including a portion of which an area is the largest.

FIG. 2B is a top view of the laser irradiation surface 61 (wide surface 66). In a normal method, as illustrated by a laser scanning path 55 which is represented by a dotted line, the laser irradiation surface 61 is irradiated with the laser.

As one of the problems of the laser powder layer laminating molding method, there is warp deformation which is generated at the time of forming the plate-shaped layer laminating molded object. Contraction of the molded object is generated when the material powder is melted and sintered, and when the molded object which is melted and sintered is cooled.

As illustrated in FIGS. 1A to 1D, since the three-dimensional shape is obtained by sequentially repeating the melting and the sintering of the material powder in the laser powder layer laminating molding method, contractive force is accumulated as residual stress due to the contraction of the molded object described above, and the warp deformation is generated. Such warp deformation is more likely to be generated as the contractive force due to the melting and the sintering of the material powder is large. Accordingly, the warp deformation is likely to be generated as the laser irradiation area of the molded object is large. Even in the same laser irradiation area, the warp tends to be great as a layer laminating thickness of the molded object is small. Therefore, there a high probability that the warp deformation is particularly generated at the time of manufacturing the plate-shaped layer laminating molded object as illustrated in FIGS. 2A and 2B.

In order to prevent the warp deformation as described above, in Example 1, the laser irradiation surface 61 of the plate-shaped layer laminating molded object 60 is divided into a plurality of small regions. In the related art, when the plate-shaped molded object is molded using the laser powder layer laminating molding method as illustrated in FIG. 2A, the material powder is irradiated with the laser in accordance with the laser scanning path as illustrated in FIG.

2B. In such a laser irradiation method and such a layer laminating molded object structure, since the area to be melted and sintered at a time with the laser is large, the contractive force at the time of the molding becomes large, and it is difficult to prevent the warp deformation.

FIG. 3A illustrates an example of the scanning path in a laser scanning treatment which is proposed in Example 1. In the laser irradiation method and the layer laminating molded object structure which are proposed in Example 1, the laser irradiation surface 61 is divided into small regions 62, and the laser irradiation is performed per small region 62. For example, the laser scanning of the small regions 62 is performed one by one, in sequence of b, c, and d from a small region 62a on the left side of FIG. 3A. A scanning sequence is not limited, and the laser scanning may be performed in sequence of d, b, and c from the small region 62a on the left side of FIG. 3A.

In this manner, since the area to be melted and sintered at a time becomes small, it is possible to reduce the contractive force and the warp deformation. For example, as a laser scanning path in a case where the laser irradiation surface 61 is divided into the small regions 62, the laser scanning path 55 which is represented by the dotted line in FIG. 3A may be used. In FIG. 3A, the laser scanning path 55 of the same pattern is used in all small regions, but the laser scanning paths which are different from each other may be used per small region 62.

FIG. 3B is an external top view of the molded object, which is obtained by the laser scanning method in which the laser irradiation surface 61 is divided into the small regions. The small regions 62 individually pass through a heating and cooling process, as a result, a micro discontinuity surface is formed, thereby, a boundary 63 is formed. Between the small regions 62, it is possible to confirm the boundary 63 with the naked eye. The division is not limited to the division in one direction as illustrated in FIG. 3A, and the division may be two-dimensionally performed as illustrated in FIG. 3B.

FIG. 3C is an external top view of the molded object illustrating an example of other dividing methods. As illustrated in FIG. 3C, a method for two-dimensionally dividing a whole of the laser irradiation surface 61 is considered. The molded object is not limited to a rectangle. The sizes of the small regions 62 may not necessarily be equal. The shape of the small region 62 may not necessarily be rectangular.

Example 2

Example 2 will be described, using FIG. 4. An item which is described in Example 1, and is not described in Example 2 is applicable to Example 2 unless there is a special circumstance.

FIG. 4A is a top view illustrating an example of the laser scanning path 55 in a laser scanning treatment which is proposed in Example 2. In Example 2, as illustrated in FIG. 4A, the laser irradiation surface 61 of the plate-shaped layer laminating molded object 60 is divided into a plurality of small regions 62e to 62i which are different from each other in size. Here, the "size" refers to at least one of dimensions such as the area, a length of a side, and the like. According to a configuration of Example 2, it is possible to reduce the warp of the plate-shaped layer laminating molded object with the number of divisions which is smaller than ever, in addition to effects of Example 1.

As described above, in the laser powder layer laminating molding method, as the area to be melted and sintered at a time with the laser is large, the contractive force at the time of the molding becomes large, and the warp deformation is likely to be generated. Therefore, in a case of the same laser irradiation area, a reduction effect of the warp is large as the number of divisions becomes large. On the other hand, as the number of divisions is large, since more time is necessary for the laser irradiation, the manufacturing time of the layer laminating molded object becomes long. Therefore, from the viewpoint of mass production, it is desirable to obtain the warp reduction effect with the number of divisions as small as possible.

Generally, in the plate-shaped layer laminating molded object, a warp deformation amount tends to be large as an outside of the laser irradiation surface. Therefore, when the laser irradiation surface is divided, basically, as illustrated in FIG. 4A, the large warp reduction effect is obtained with the small number of divisions as a whole, in a case where the outside (or an end portion) is finely divided in comparison with an inside.

FIG. 4B is a top view illustrating an example of a case of being two-dimensionally divided into the small regions 62. Even in the example of FIG. 4B, the outside is finely divided, thereby, the large warp reduction effect is obtained with the small number of divisions.

Figure 4C:
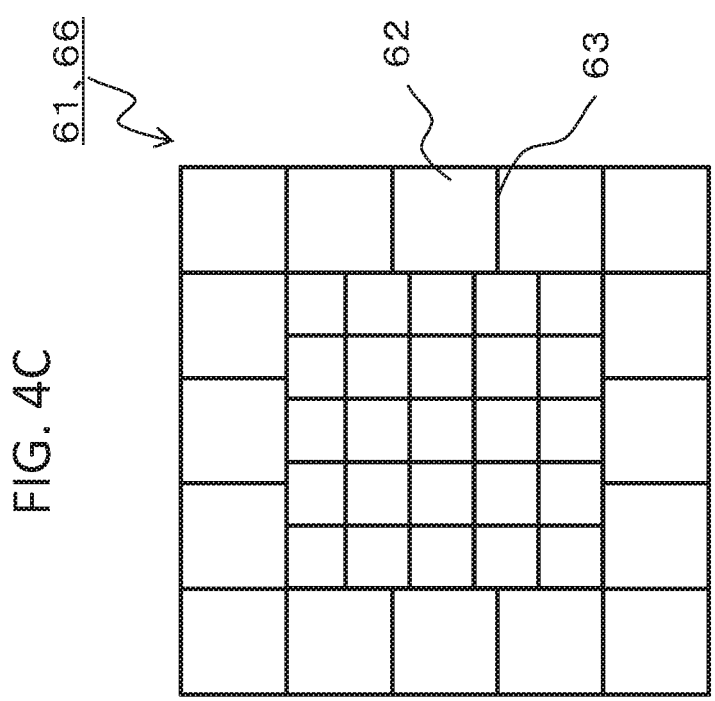
FIG. 4C is a top view for describing the structure of the molded object according to Example 2.

FIG. 4C is a top view illustrating another example. Depending on the shape of the molded object, as illustrated in FIG. 4C, there is a case where the warp reduction effect is obtained by finely dividing the inside in comparison with the outside. For example, this is a case where the layer laminating thickness of the inside of the laser irradiation surface is large in comparison with the outside. Therefore, depending on the shape of the molded object, the inside may be finely divided in comparison with the outside of the laser irradiation surface.

Example 3

Example 3 will be described, using FIG. 5. The item which is described in Example 1 and Example 2, and is not described in Example 3 is applicable to Example 3 unless there is the special circumstance. FIG. 5 is a sectional view of the plate-shaped layer laminating molded object 60. FIG. 5 is the sectional view, but an oblique line is not applied thereto in order to easily understand features of the structure.

In Example 3, as illustrated in FIG. 5, the boundary 63 (N) between the small regions 62 (N) obtained by dividing the laser irradiation surface 61 (N) of an N-th layer (the lowermost layer is referred to as a first layer) which forms the plate-shaped layer laminating molded object 60, overlaps at least one of the small regions 62 (N+1) obtained by dividing the laser irradiation surface 61 (N+1) of an N+1-th layer and the small regions 62 (N−1) obtained by dividing the laser irradiation surface 61 (N−1) of an N−1-th layer. That is, the boundary 63 between the small regions is made in a structure in which continuing on two or more layers in a layer laminating direction is avoided.

According to a configuration of Example 3, it is possible to prevent the strength lowering of the molded object, which is generated by dividing the laser irradiation surface, while reducing the warp deformation of the plate-shaped layer laminating molded object, in addition to the effects of Example 1 and Example 2.

As described above, in the laser powder layer laminating molding method, the laser irradiation surface of the plate-shaped layer laminating molded object 60 is divided into the small regions 62, thereby, it is possible to reduce the warp deformation. On the other hand, in a case where the laser irradiation surface is divided into the small regions, since the boundary between the small regions becomes a starting point of destruction, the strength is greatly lowered in comparison with a case of being not divided. Therefore, in order to prevent the strength lowering, for example, as illustrated in FIG. 5, the configuration in which the position of the boundary 63 (N) between the small regions obtained by dividing the laser irradiation surface 61 (N) of the N-th layer overlaps the small regions 62 (N+1) obtained by dividing the laser irradiation surface 61 (N+1) of the N+1-th layer, thereby, the boundaries 63 between the small regions 62 which exist on each laser irradiation surface do not match up, is effective. In this manner, the boundaries between the small regions do not match up, thereby, it is possible to prevent a phenomenon that the boundary becomes the starting point of the destruction, and the whole of the molded object is destroyed.

Example 4

Example 4 will be described, using FIG. 6. The item which is described in Example 1 to Example 3, and is not described in Example 4 is applicable to Example 4 unless there is the special circumstance. FIG. 6 is a sectional view of the plate-shaped layer laminating molded object 60. FIG. 6 is the sectional view, but the oblique line is not applied thereto in order to easily understand the features of the structure.

In Example 4, as illustrated in FIG. 6, the number of the small regions 62 obtained by dividing the laser irradiation surface 61 (N) of the N-th layer which forms the plate-shaped layer laminating molded object 60 is smaller than the number of the small regions 62 (N+1) obtained by dividing the laser irradiation surface 61 (N+1) of the N+1-th layer. According to a configuration of Example 4, it is possible to reduce the warp of the plate-shaped layer laminating molded object with the number of divisions which is smaller than ever, in addition to the effects of Example 1 to Example 3.

In the laser powder layer laminating molding method, the warp deformation is likely to be generated in a case where the area to be melted and sintered at a time with the laser is large, meanwhile, the warp is less likely to be generated as the layer laminating thickness is large. Therefore, when the plate-shaped layer laminating molded object is molded, the reduction effect of the warp is high in a case where the laser irradiation surface which is sintered at an initial stage of the molding is finely divided, in comparison with a case where the surface which is sintered at a later stage of the molding is finely divided. Accordingly, as illustrated in FIG. 6, by making the number of divisions small as the surface which is molded later, the reduction effect of the warp is obtained, with the number of divisions which is smaller than ever as a whole of the molded object.

Example 5

Example 5 will be described, using a side view of the plate-shaped layer laminating molded object 60 illustrated in FIG. 7. The item which is described in Example 1 to Example 4, and is not described in Example 5 is applicable to Example 5 unless there is the special circumstance. FIG. 7 is a sectional view of the plate-shaped layer laminating molded object 60. FIG. 7 is the sectional view, but the oblique line is not applied thereto in order to easily understand the features of the structure.

In Example 5, as illustrated in FIG. 7, the surface (the wide surface, hereinafter) 66 including a portion of which the area is the largest in the plate-shaped layer laminating molded object 60 inclines towards the laser irradiation surface 61. According to a configuration of Example 5, it is possible to further reduce the warp of the plate-shaped layer laminating molded object 60, in addition to the effects of Example 1 to Example 4.

As described above, in the laser powder layer laminating molding method, as the area to be melted and sintered at a time with the laser is large, the contractive force at the time of the molding becomes large, and the warp deformation is likely to be generated. Therefore, since it is possible to reduce the size of the laser irradiation surface in comparison with a case where the wide surface and the laser irradiation surface match up by causing the wide surface 66 of the same plate-shaped layer laminating molded object to incline towards the laser irradiation surface 61, the further reduction effect of the warp is expected.

However, as the wide surface 66 of the plate-shaped layer laminating molded object inclines towards the laser irradiation surface 61, the number of laminating layers which is necessary for the molding is increased, and the manufacturing time of the molded object becomes long. An influence on the manufacturing time due to the increase in the number of laminating layers is far greater in comparison with the influence due to the increase in the number of divisions of the laser irradiation surface. Therefore, in reality, it is desirable to obtain the further large reduction effect of the warp by keeping an inclination angle with respect to the laser irradiation surface of the wide surface in the scope of 10 degrees or less, and using together with the division of the laser irradiation surface.

Example 6

Example 6 will be described, using FIG. 8 and FIG. 9. The item which is described in Example 1 to Example 5, and is not described in Example 6 is applicable to Example 6 unless there is the special circumstance. Example 6 relates to a structure of a ridge filter that is used in a particle system for medical use. In the particle system for the medical use, for the purpose of controlling energy distribution in a depth direction of a particle beam, a repeated structure body which is referred to as a ridge filter is used.

In order to enhance properties of the ridge filter, there is a need to use a complicated structure onto which the mechanical machining is less likely to be performed, but a three-dimensional layer laminating molding method such as the laser powder layer laminating molding method is used, thereby, it is possible to perform the manufacturing even in a case where the mechanical machining of the related art is less likely to be performed.

Figure 8:
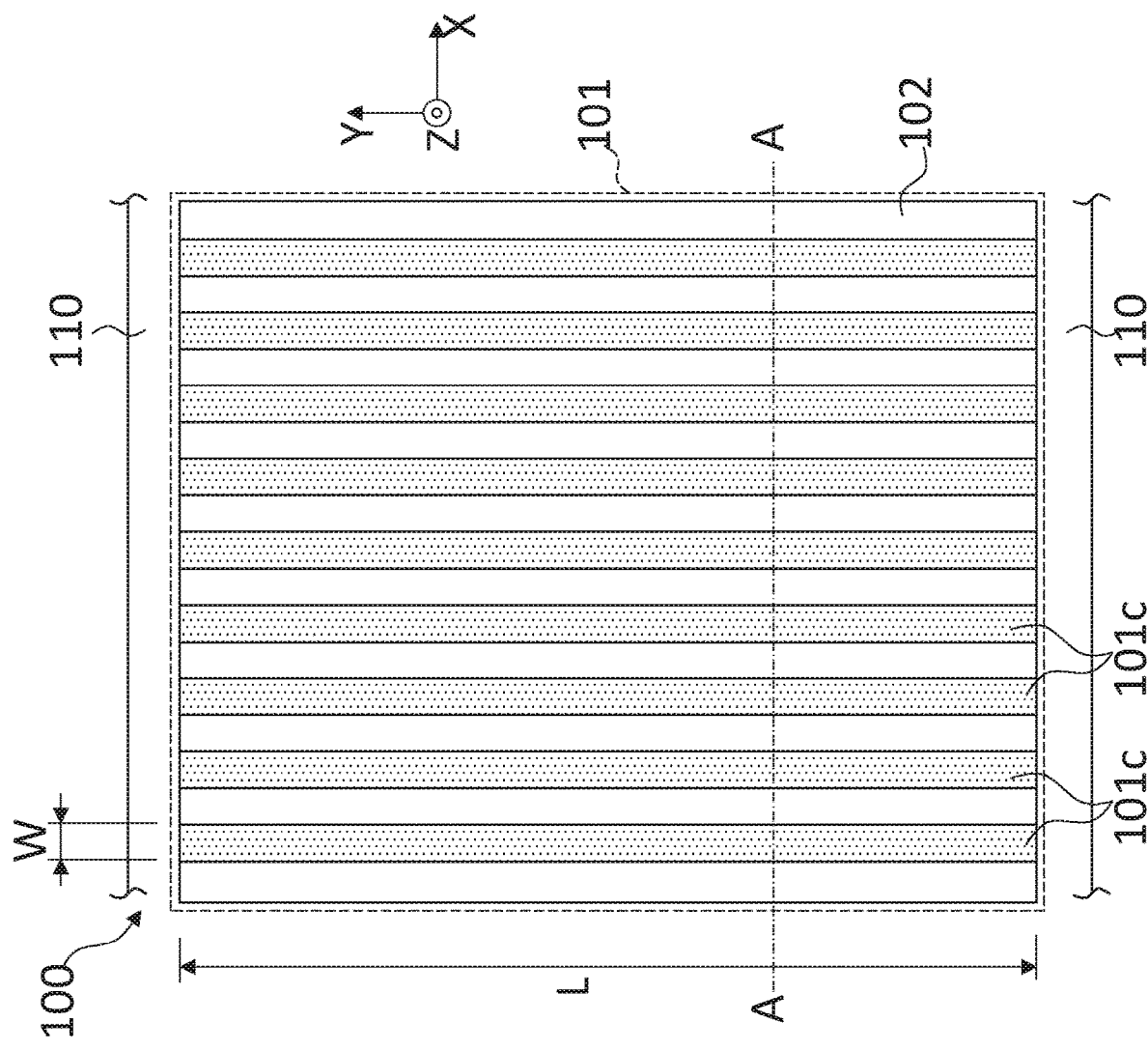
FIG. 8 is a plan view illustrating an example of a structure of a ridge filter according to Example 6.

FIG. 8 illustrates a top view of the ridge filter. As illustrated in FIG. 8, in a ridge filter 100, a repeated structure body (first structure body) 101 having a width W is formed on a bottom plate (second structure body) 102 that is mounted in a frame 110. In the repeated structure body 101, an extending portion 101c which extends in a Y direction forms a repeated structure.

Figure 9:
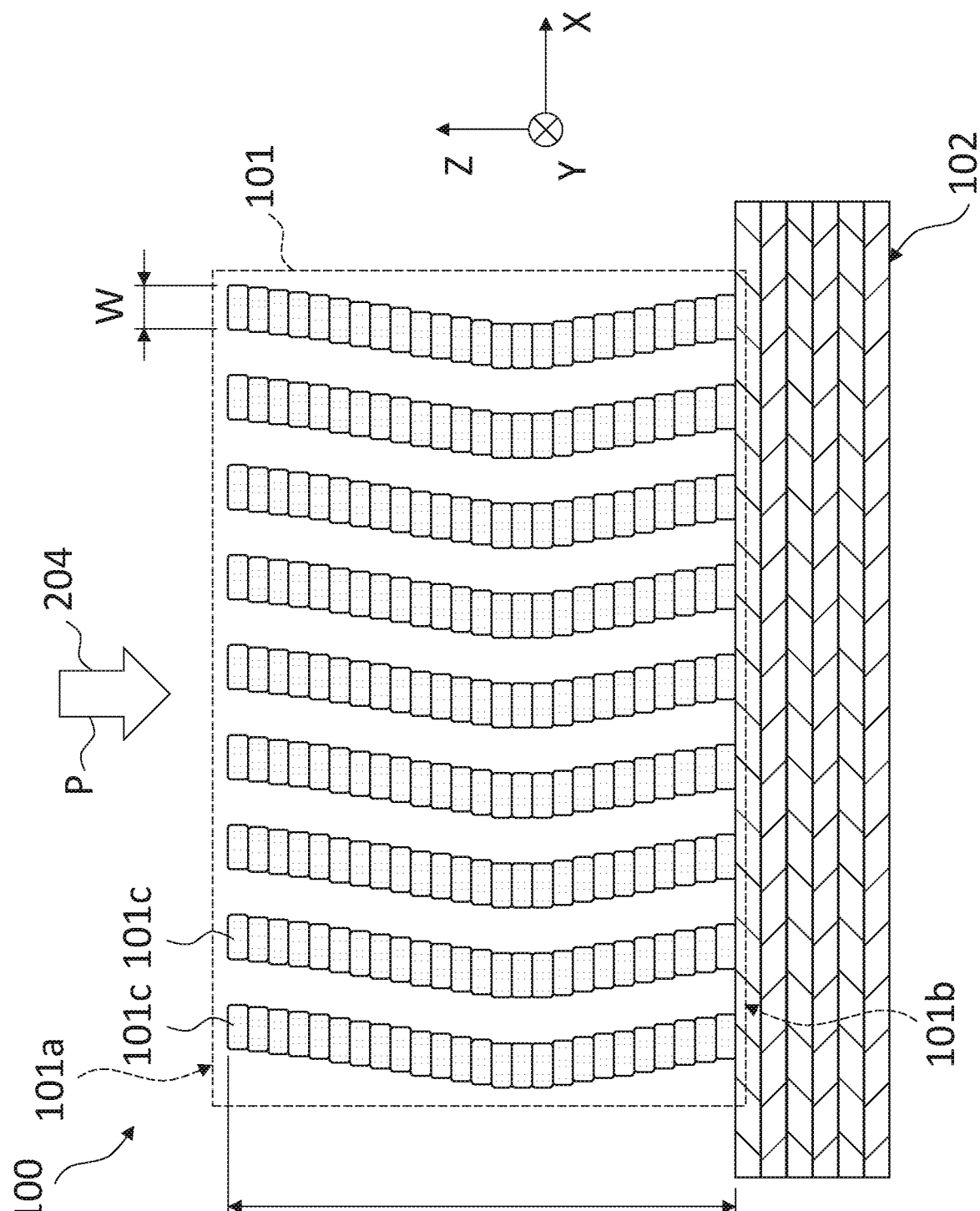
FIG. 9 is a sectional view illustrating a structure obtained by cutting the ridge filter along A-A line in FIG. 8.

FIG. 9 illustrates a sectional view of the ridge filter taken along A-A position in FIG. 8. In order to manufacture the ridge filter by the laser powder layer laminating molding method descried above, first, the layers of the bottom plate 102 illustrated in FIG. 9 are laminated and molded. Next, a plurality of extending portions 101c which are respectively formed of a layer laminating body with respect to a direction (X direction or Y direction) intersecting with the layer laminating direction (Z direction) of the bottom plate 102, and extend in the layer laminating direction, are formed on the bottom plate 102. Since the extending portion 101c is configured in a shape which is bent in the layer laminating direction, the manufacturing is less likely to be performed by the mechanical machining of a bulk material.

In this manner, the repeated structure body 101 including the plurality of extending portions 101c are molded. Thereby, the ridge filter 100 in which each of the bottom plate 102 and the repeated structure body 101 is formed of the layer laminating body, and the bottom plate 102 and the repeated structure body 101 are integrally formed, is formed. 101a indicates an upper surface of the repeated structure body 101, and 101b indicates a lower surface of the repeated structure body 101. The irradiation with a particle beam 204 of a proton P or the like which is toward the lower surface 101b from the upper surface of the structure body 101 is performed, and is filtered.

The bottom plate 102 and the repeated structure body 101 are integrally formed, thereby, it is possible to improve rigidity of the ridge filter 100, and it is possible to prevent the repeated structure body 101 from bending due to external force or empty weight after the molding.

On the other hand, since the bottom plate 102 is a plate-shaped layer laminating molded object of which dimensions are large in the X direction and the Y direction, and the dimension is small in the Z direction, there is a concern that the warp deformation is generated due to the material contraction at the time of the user sintering.

Therefore, in Example 6, the laser irradiation surface 61 of the bottom plate 102, which forms the ridge filter 100, and is formed integrally with the repeated structure body 101, is divided into a plurality of small regions 62. That is, the bottom plate 102 is formed into the layer laminating structure described in Examples 1 to 5, by the laser powder layer laminating molding method. According to a configuration of Example 6, when the ridge filter 100 is molded by using the laser powder layer laminating molding method, it is possible to prevent that the warp deformation is generated n the bottom plate 102.

As described above, in the powder layer laminating molded object, the layer laminating molding method, and the ridge filter of the examples, the powder layer is sintered by irradiating the thermoplastic resin powder layer with the laser beam or the like, thereafter, when the forming and the sintering of the powder layer are sequentially repeated, the laser irradiation surface of the laser powder layer laminating molded object is divided into the plurality of small regions.

The present invention is not limited to the embodiments described above, but includes various modification example. For example, it is possible to replace a portion of the configuration of one example with the configurations of other examples, and it is possible to add the configurations of other examples to the configuration of one example. Moreover, it is possible to add, delete, or replace the configurations of other examples, with respect to a portion of the configuration of each example.

REFERENCE SIGNS LIST

10: material powder
20: part bed portion
30a: left side feed portion
30b: right side feed portion
40: roller
50: sintered body of first layer
51: sintered body of second layer
60: plate-shaped layer laminating molded object
61: laser irradiation surface
62: small region
63: boundary between small regions
64: laser irradiation surface of N-th layer
65: laser irradiation surface of N+1-th layer
66: wide surface (surface including a portion of which an area is largest in the plate-shaped layer laminating molded object)
100: ridge filter
101: repeated structure body (first structure body)
101a: upper surface
101b: lower surface
101c: extending portion
102: bottom plate (second structure body)
110: frame
204: particle beam

The invention claimed is:

1. A layer laminating molded object which has a layer laminating structure of a sintered body layer of thermoplastic resin powder,
wherein the sintered body layer is divided into a plurality of small regions within a surface of the layer, and
wherein the sintered body layer is divided into the plurality of small regions having two different sizes including a first size of a first plurality of small regions around a perimeter of the sintered body layer and a second size of a second plurality of small regions disposed inside of the first plurality of small regions, wherein the first size is smaller than the second size.

2. The layer laminating molded object according to claim 1,
wherein at least one of the small regions obtained by dividing an outside of the sintered body layer is larger than at least one of the small regions obtained by dividing an inside of the sintered body layer in size.

3. The layer laminating molded object according to claim 1,
wherein at least one of the small regions obtained by dividing the sintered body layer of an N+1-th layer and the small regions obtained by dividing the sintered body layer of an N−1-th layer overlaps a boundary of the small regions obtained by dividing the sintered body layer of an N-th layer.

4. The layer laminating molded object according to claim 1,
wherein the number of the small regions obtained by dividing the sintered body layer of the N−1-th layer is larger than the number of the small regions obtained by dividing the sintered body layer of the N-th layer.

5. The layer laminating molded object according to claim 1,
wherein the sintered body layer inclines towards a surface including a portion of which an area is the largest in the layer laminating molded object.

6. The layer laminating molded object according to claim 1,
wherein the sintered body layer contains a crystalline resin.

* * * * *